United States Patent
Zhang et al.

(10) Patent No.: US 11,215,626 B2
(45) Date of Patent: Jan. 4, 2022

(54) GATE SYSTEM FOR SAMPLE DETECTION AND METHOD OF SAMPLE INSPECTION

(71) Applicants: TSINGHUA UNIVERSITY, Beijing (CN); Nuctech Company Limited, Beijing (CN)

(72) Inventors: Qingjun Zhang, Beijing (CN); Yuanjing Li, Beijing (CN); Zhiqiang Chen, Beijing (CN); Ziran Zhao, Beijing (CN); Yinong Liu, Beijing (CN); Yaohong Liu, Beijing (CN); Qiufeng Ma, Beijing (CN); Lili Yan, Beijing (CN); Weiping Zhu, Beijing (CN); Biao Cao, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 95 days.

(21) Appl. No.: 16/406,272

(22) Filed: May 8, 2019

(65) Prior Publication Data
US 2019/0346472 A1    Nov. 14, 2019

(30) Foreign Application Priority Data
May 9, 2018  (CN) .......................... 201810437372.9

(51) Int. Cl.
*G01N 35/04*  (2006.01)
*G01N 25/54*  (2006.01)
(Continued)

(52) U.S. Cl.
CPC ............. *G01N 35/04* (2013.01); *G01N 25/54* (2013.01); *G01N 35/1095* (2013.01);
(Continued)

(58) Field of Classification Search
CPC .......... G01N 2001/028; G01N 35/004; G01N 35/1095; G01N 25/44; G01N 2001/022;
(Continued)

(56) References Cited

U.S. PATENT DOCUMENTS 3,572,128 A * 3/1971 Hemeon ................. G01N 1/04
73/863.24
4,848,165 A * 7/1989 Bartilson ................ G01N 1/04
73/864.71
(Continued)

FOREIGN PATENT DOCUMENTS

CN    206235468 U    6/2017
GB    2262603 A *    6/1993  ........... G01N 1/2205
(Continued)

*Primary Examiner* — Alexander A Mercado
(74) *Attorney, Agent, or Firm* — Scully Scott Murphy & Presser

(57) ABSTRACT

The present disclosure provides a gate system for sample detection and a method of sample inspection, which relate to the field of detection and analysis technology. The gate system comprises: an accommodating apparatus configured to accommodate an inserted ticket to be detected; a wipe sampling apparatus including a wipe sampling belt which is configured to drive the ticket to be detected to move within the accommodating apparatus and to conduct a wipe sampling to the ticket; an inspiratory sampling apparatus configured to collect samples dropped from the wipe sampling apparatus; and a detection apparatus configured to detect the samples and output detection results. The gate system for sample detection and the method of sample inspection provided by the present disclosure have a wide range of applications and can perform rapid sampling and detection to those substances that are difficult to be volatilized.

9 Claims, 4 Drawing Sheets

(51) Int. Cl.
*G01N 35/10* (2006.01)
*G01N 35/00* (2006.01)
*G01N 1/02* (2006.01)

(52) U.S. Cl.
CPC ............ *G01N 2001/028* (2013.01); *G01N 2035/00445* (2013.01); *G01N 2035/0484* (2013.01); *G01N 2035/1048* (2013.01)

(58) Field of Classification Search
CPC . G01N 2035/1048; G01N 2035/00445; G01N 2035/0484; G01N 33/227; G01N 1/02; G01N 27/622; G01N 30/02; G01N 30/72; G07C 9/00896
See application file for complete search history.

(56) References Cited

U.S. PATENT DOCUMENTS

| | | | | |
|---|---|---|---|---|
| 5,741,984 | A * | 4/1998 | Danylewych-May | A61B 10/0096 73/864 |
| 6,874,685 | B1 * | 4/2005 | Moreau | G07C 9/10 235/384 |
| 7,116,798 | B1 * | 10/2006 | Chawla | G01N 33/0057 382/100 |
| 9,214,324 | B2 * | 12/2015 | Nagano | H01J 49/0459 |
| 10,151,671 | B2 * | 12/2018 | Zhang | G01N 30/30 |
| 10,281,431 | B2 * | 5/2019 | Zhang | G01N 27/622 |
| 2003/0106362 | A1 * | 6/2003 | Megerle | G01N 1/22 73/23.2 |
| 2004/0124352 | A1 * | 7/2004 | Kashima | H01J 49/049 250/288 |
| 2004/0227073 | A1 * | 11/2004 | Krasnobaev | G01N 27/622 250/288 |
| 2006/0042407 | A1 * | 3/2006 | Napoli | G01N 27/622 73/863.12 |
| 2007/0086925 | A1 * | 4/2007 | O'Donnell | G01N 33/0057 422/82.05 |
| 2008/0217524 | A1 * | 9/2008 | Mawer | G01N 1/02 250/281 |
| 2008/0264186 | A1 * | 10/2008 | Nacson | G01N 1/02 73/863.12 |
| 2009/0044641 | A1 * | 2/2009 | Konduri | G01N 1/2273 73/863.11 |
| 2009/0050801 | A1 * | 2/2009 | Fedorov | H01J 49/066 250/288 |
| 2010/0126284 | A1 * | 5/2010 | Boudries | G01N 1/405 73/863.12 |
| 2011/0159596 | A1 * | 6/2011 | Keinan | G01N 1/2211 436/52 |
| 2014/0151543 | A1 * | 6/2014 | Nagano | H01J 49/04 250/282 |
| 2014/0345364 | A1 * | 11/2014 | Lin | G01N 27/622 73/28.01 |
| 2015/0241401 | A1 * | 8/2015 | Wu | G01N 1/02 435/30 |
| 2018/0080855 | A1 * | 3/2018 | Taylor | C08L 101/00 |
| 2019/0205709 | A1 * | 7/2019 | Ho | H01R 12/51 |
| 2019/0368976 | A1 * | 12/2019 | Blair | G01N 33/227 |

FOREIGN PATENT DOCUMENTS

| | | |
|---|---|---|
| JP | 2004-535563 A | 11/2004 |
| JP | 2017-215174 A | 12/2017 |
| WO | 2012/063796 A1 | 5/2012 |

* cited by examiner

GATE SYSTEM FOR SAMPLE DETECTION AND METHOD OF SAMPLE INSPECTION

CROSS REFERENCE

This application is based upon and claims priority to Chinese Patent Application No. 201810437372.9, filed on May 9, 2018, which is incorporated herein by reference in its entirety.

TECHNICAL FIELD

The present disclosure relates to the technology field of detection and analysis in particular, to a gate system for sample detection and a method of sample inspection.

BACKGROUND

In order to combat terrorist activities and drug smuggling, at present, trace drugs and explosives are mainly detected by technologies such as ion mobility spectrometry, gas chromatography, gas chromatography-ion mobility spectrometry, and gas chromatography-mass spectrometry, etc. In many occasions such as imports and exports of airports, railways, highways, conference hall, there is an urgent need to provide an apparatus that can quickly, efficiently collect and analyze those high boiling-point, nonvolatile samples including trace drugs and explosives, for a ticket, an IC card or an ID card.

Currently existing detection of trace drugs and explosives is mainly performed by surface sampling, specifically by wiping clothes and luggage of the object to be inspected with test belts, and then the sample is thermal desorbed for an instrumental analysis. But there are few reports on those techniques that are suitable for sampling and analysis of drugs, explosives or the like on the ticket, the IC card or the ID card. Among which Smiths has disclosed a method of inhaling with a gas pump and adsorption sampling with an adsorption belt. Hitachi has reported a method of sampling by purging surfaces of certificate/papers using a fan-shaped beam airflow in combination with a tornado inspiratory technique. These techniques can realize sampling and testing to the ticket, the IC card, the ID card, etc., while they exhibit relative low sampling efficiencies, and require high detection sensitivity of the instrument, and thus are difficult to implement.

In an existing sample capturing and sample analyzing apparatus, a sample capturing part is equipped with a sampling belt wound on two spools, with an adsorbent material coated on the sampling belt. When sampling, a pump is started to inhale so as to draw the samples onto the sampling belt and to be absorbed. After the sampling is completed, the part on which the samples are adsorbed is transferred to a thermal desorption region for instantaneous desorption and then is sent to the GC-IMS for detection and analysis. This technology can realize an automatic and continuous sampling, which is suitable for the sampling and detection to a card, a certificate or the like. However, it essentially belongs to an inspiratory (or inhalation) type of sampling. This sampling method exhibits a relative low efficiency in collecting samples of drugs and explosives with high boiling point and strong adhesion.

In an existing gate safety inspection apparatus, the gate safety inspection apparatus is operated by using a fan-shaped beam airflow to purge the surfaces of the card and certificate, as well as a tornado inspiratory sampling device to collect the samples dropped from the cards and certificate which, and finally sending the samples to a detection apparatus for detecting. In comparison to the direct inhalation sampling, this method of purging the surfaces of the cards and certificate with a powerful fan-shaped beam airflow in combination with the tornado inspiratory sampling exhibit a significant improvement in sampling effect. However, while the samples are blown down off the cards and certificate and are captured by a tornado sampling device, a considerable part of the sample that is blown down off may be lost as it fails to be captured by the tornado sampling apparatus Moreover, those high-boiling particles such as drugs and explosives may not be easily shot down by airflow as being adsorbed by the cards and certificate. Therefore, even for such a sampling technology, the sampling effect on drugs and explosives is difficult to further improve.

Therefore, there is a need for a new gate system for sample detection and a new method of sample inspection.

The above information disclosed in this Background Section is only to facilitate understanding of the background of the present disclosure, and thus it may include information that does not constitute the prior art known to those of ordinary skill in the art.

SUMMARY

In view of this, the present disclosure provides a gate system for sample detection and a method of sample inspection, which have a wide range of applications and can take rapid sampling and detection of non-volatile substances or those substances that are not easily volatilized.

Other features and advantages of the present disclosure will become apparent from the following detailed description, or partly acquired from the practice of the present disclosure.

According to the first aspect of the present disclosure, a gate system for sample detection is provided, the gate system for sample detection comprises: an accommodating apparatus configured to accommodate an inserted ticket to be detected; a wipe sampling apparatus including a wipe sampling belt which is configured to drive the ticket to be detected to move within the accommodating apparatus and to conduct a wipe sampling (or swab sampling) on the ticket to be detected; an inspiratory sampling apparatus configured to collect samples dropped from the wipe sampling apparatus; and a detection apparatus configured to detect the samples and output detection results.

In an exemplary embodiment of the present disclosure, the accommodating apparatus comprises a card slot configured to carry the ticket to be detected.

In an exemplary embodiment of the present disclosure, the accommodating apparatus further comprises a spring top bead configured to increase a contact pressure between the ticket to be detected and a wipe sampling belt to make the ticket to be detected in contact with the wipe sampling belt.

In an exemplary embodiment of the present disclosure, the accommodating apparatus further comprises: an information reader configured to read information of the ticket to be detected by a built-in chip and to perform information verification; and a spring plate configured to pop up the ticket to be detected from the card slot after the information verification of the ticket to be detected is completed.

In an exemplary embodiment of the present disclosure, the wipe sampling apparatus further comprises: an electric roller configured to drive the wipe sampling belt for transmission; and a semiconductor refrigeration chip configured to cool the wipe sampling belt.

In an exemplary embodiment of the present disclosure, the inspiratory sampling apparatus comprises: a sampling inspiratory port provided under the wipe sampling apparatus, and configured to draw the samples into the inspiratory sampling apparatus; airflow discharge ports configured to form airflows; and a sampling head configured to collect the samples.

In an exemplary embodiment of the present disclosure, the airflow discharge ports comprise a central rotary airflow discharge port and a peripheral rotary airflow discharge port.

In an exemplary embodiment of the present disclosure, the central rotary airflow discharge port surrounds the sampling inspiratory port for discharging a low-speed airflow with a first flow rate; and the peripheral rotary airflow discharge port surrounds the central rotary airflow discharge port for discharging a high-speed airflow with a second flow rate higher than the first flow rate.

In an exemplary embodiment of the present disclosure, the inspiratory sampling apparatus further comprises an O-ring seal and a flared sampling head cover.

In an exemplary embodiment of the present disclosure, the inspiratory sampling apparatus comprises a tornado sampling apparatus.

In an exemplary embodiment of the present disclosure, the detection apparatus comprises at least one of a chromatographic column and an ion migration tube, and a sample exchange semi-permeable membrane.

According to the second aspect of the present disclosure, a method of sample inspection is provided, the method comprises receiving a ticket to be detected, conducting a wipe sampling to the ticket to be detected with a wipe sampling belt in a wipe sampling apparatus, blowing down samples from the wipe sampling belt by air flow and collecting the samples dropped from the wipe sampling belt, and detecting the samples, and outputting detection results.

In an exemplary embodiment of the present disclosure, after receiving the ticket to be detected, reading and verifying information of the ticket to be detected within a accommodating apparatus by a gate system; wherein, the gate system comprises a accommodating apparatus configured to accommodate an inserted ticket to be detected, a wipe sampling apparatus including a wipe sampling belt which is configured to drive the ticket to be detected to move within the accommodating apparatus and to conduct a wipe sampling on the ticket to be detected, an inspiratory sampling apparatus configured to collect samples dropped from the wipe sampling apparatus, and a detection apparatus configured to detect the samples and output detection results.

The gate system for sample detection and the method of sample inspection according to the present disclosure have a wide range of applications and can perform rapid sampling and detection of non-volatile substances or those substances that are not easily volatilized.

It should be understood that the above general description and the following detailed description are merely exemplary and are not intended to limit the present disclosure.

BRIEF DESCRIPTION OF THE DRAWINGS

By describing exemplary embodiments of the present disclosure in detail with reference to the accompanying drawings, these and other objectives, features and advantages of the present disclosure will become more apparent. The drawings as described in the following description are only of some embodiments of the present disclosure, and from these drawings, those of ordinary skill in the art may acquire other drawings without paying out inventive works.

DETAILED DESCRIPTION

Figure 1:
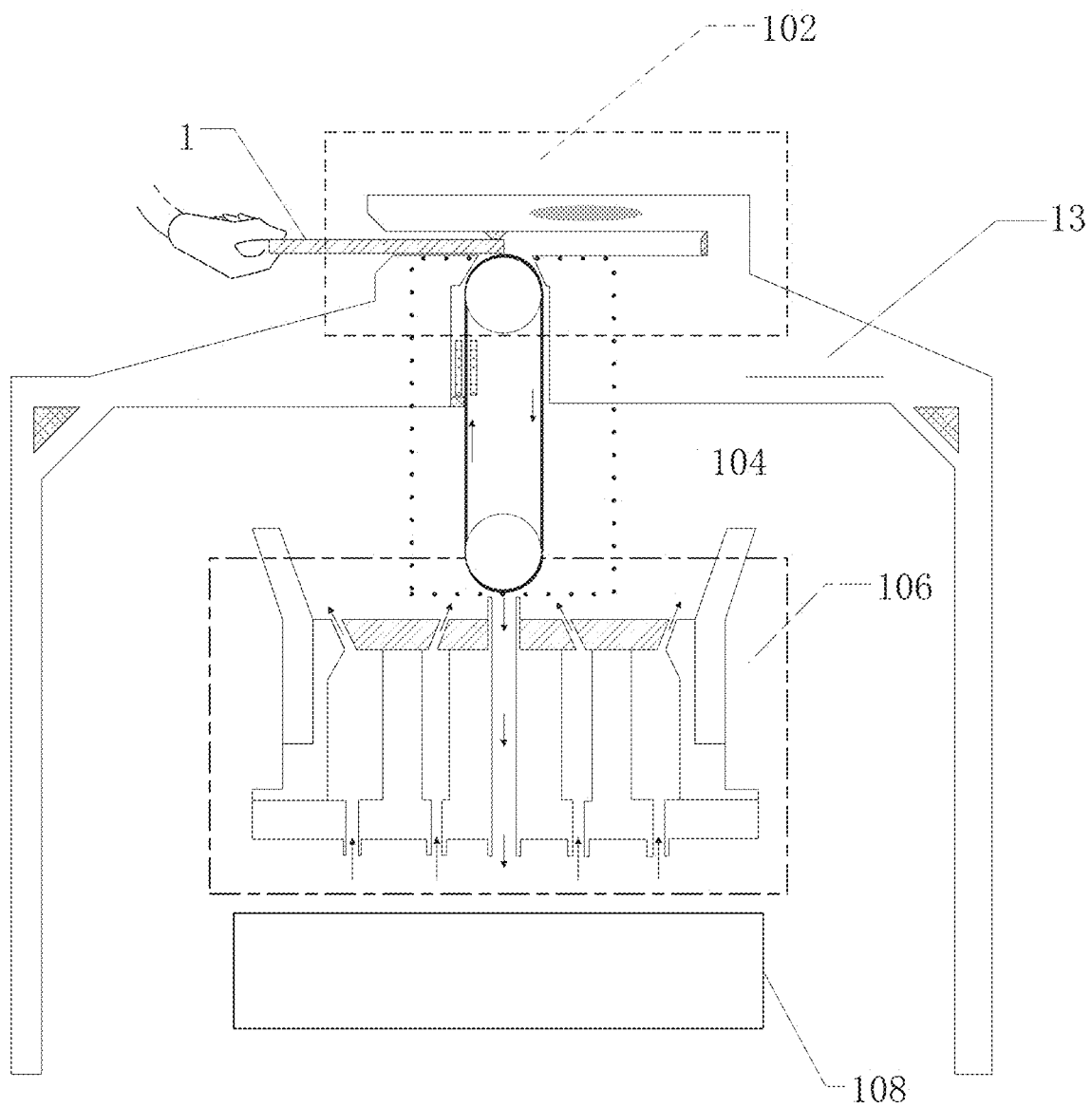
FIG. 1 illustrates a schematic diagram of a gate system for sample detection according to an exemplary embodiment.

Exemplary embodiments will now be described more fully with reference to the accompanying drawings. However, the exemplary embodiments may be embodied in a variety of forms, and should not be construed as being limited to the embodiments set forth herein. Rather, these embodiments are provided so that this disclosure will be thorough and complete, and that the concept of the exemplary embodiments can be fully conveyed to those skilled in the art. The same reference numerals in the drawings denote the same or similar components, and the repetitive description thereof will be omitted.

In addition, the described features, structures, or characteristics may be combined in any suitable manner into one or more embodiments. In the following description, numerous specific details are set forth in order to provide a fully understanding of the embodiments of the disclosure. However, those skilled in the art will appreciate that the technical solution of the present disclosure may be practiced without one or more of the specific details, or other methods, components, materials, devices, steps, etc. can be used as well. In other instances, those well-known methods, apparatus, implementations or operations are not shown or described in detail to avoid obscuring those aspects of the present disclosure.

The block diagrams shown in the drawings are merely functional entities and do not necessarily have to correspond to physically separate/independent entities. That is, these functional entities may be implemented in software forms, or these functional entities may be implemented in one or more hardware modules or integrated circuits, or these functional entities may be implemented in different network and/or processor devices and/or microcontroller apparatus.

The flow chart shown in the drawings are merely exemplary illustration, and do not have to include all of the contents and operations/steps, nor have to be performed in a sequence as described. For example, some operations/steps may be broken down and some operations/steps may be combined or partly combined, so that the actual sequence of execution may be changed in different situation.

It will be understood that, although terms such as first, second, third, etc., may be used herein to describe various components, these components are not limited by these terms. Essentially, these terms are used to distinguish one component from another. Therefore, a first component discussed below may also be termed as a second component without departing from the teachings of spirit of the present disclosure. As used herein, the term "and/or" includes any of the associated listed items and all combinations of one or more of these items.

A person skilled in the art will understand that the drawings are only of schematic diagrams of exemplary embodiments, and those modules or processes illustrated in the drawings are not necessarily required to implement the present disclosure, and therefore should not be used to limit the scope of protection of the present disclosure.

An embodiments of apparatus of the present disclosure may be used to implement an embodiments of method of the present disclosure. For those details that are not disclosed in the apparatus embodiment of the present application, please refer to the embodiments of the method of the present application.

FIG. 1 illustrates a schematic diagram of a gate system for sample detection according to an exemplary embodiment. As shown in FIG. 1, the gate system for sample detection 10 includes an accommodating apparatus 102, a wipe sampling apparatus 104, an inspiratory sampling apparatus 106, and a detection apparatus 108. In FIG. 1, reference number 1 denotes a ticket to be detected, and 13 denotes an outer shell of the gate system 10.

In the embodiment, the accommodating apparatus 102 is configured to accommodate an inserted ticket to be detected, and the accommodating apparatus 102 can further be configured to read and verify the information of the ticket to be detected as inserted in the accommodating apparatus 102. In the present disclosure, the ticket to be detected may include, for example, a ticket, an IC card, and an ID card, etc.

The wipe sampling apparatus 104 includes a wipe sampling belt 1042, and the wipe sampling belt 1042 is configured to drive the ticket to be detected to move within the accommodating apparatus, and to conduct a wipe sampling on the ticket to be detected.

The inspiratory sampling apparatus 106 is configured to collect samples dropped from the wipe sampling apparatus.

The detection apparatus 108 is configured to detect the samples and output detection results.

Figure 2:
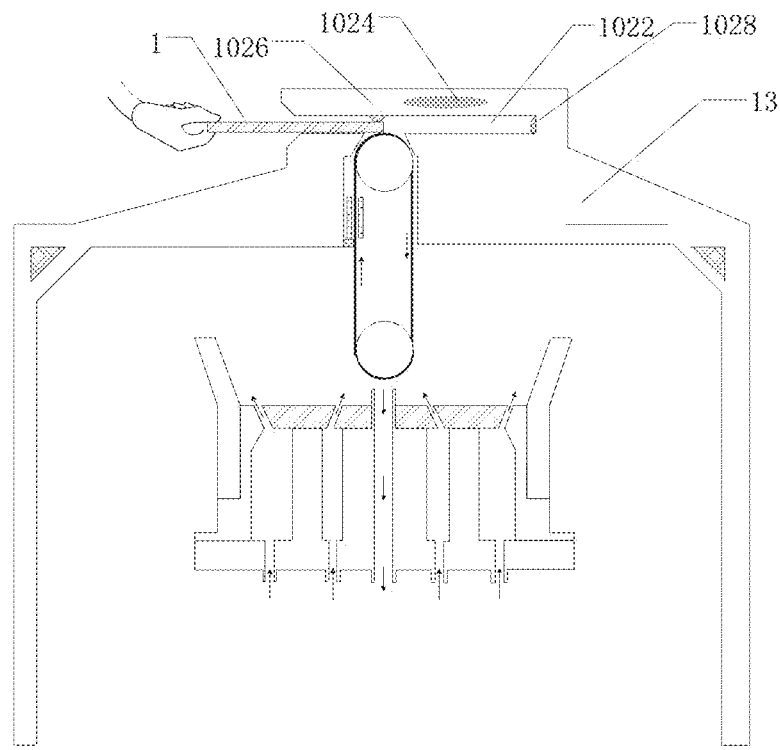
FIG. 2 illustrates a schematic diagram of an accommodating apparatus in the gate system for sample detection according to an exemplary embodiment.

FIG. 2 illustrates a schematic diagram of an accommodating apparatus in the gate system for sample detection according to an exemplary embodiment. As shown in FIG. 2, the accommodating apparatus 102 includes a card slot 1022, an information reader 1024, a spring top bead 1026, and a spring plate 1028.

In the embodiment, the card slot 1022 is configured to carry the ticket to be detected.

The information reader 1024 is configured to read, by a built-in chip, the information of the ticket to be detected, and to perform an information verification. The information reader may include, for example, an information reading chip, by which the information in a document/certificate such as a ticket, an IC card, and an ID card can be read for performing the information verification.

The spring top bead 1026 is configured to increase a contact pressure between the ticket to be detected and the wipe sampling belt so as to make the ticket to be detected come in contact with the wipe sampling belt.

The spring plate 1028 is configured to pop-up the ticket to be detected from the card slot after the information verification of the ticket to be detected is completed.

Figure 3:
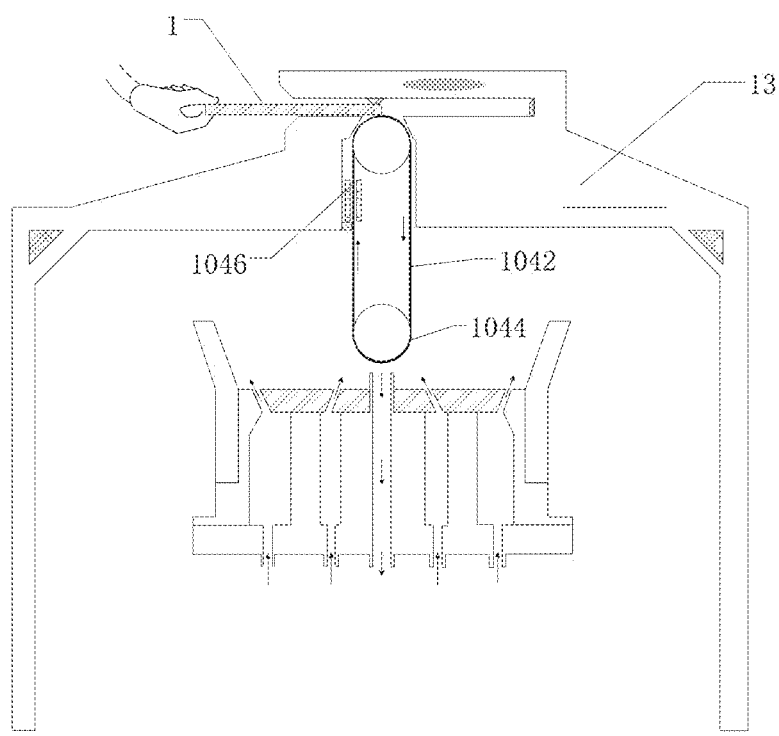
FIG. 3 illustrates a schematic diagram of a wipe sampling apparatus in the gate system for sample detection according to an exemplary embodiment.

FIG. 3 illustrates a schematic diagram of a wipe sampling apparatus in the gate system for sample detection according to an exemplary embodiment. As shown in FIG. 3, the wipe sampling apparatus 104 includes the wipe sampling belt 1042, an electric roller 1044, and a semiconductor chilling plate (cooler) 1046.

In the embodiment, the electric roller 1044 is configured to drive the wipe sampling belt for a transmission.

The semiconductor refrigeration chip is configured to cool the wipe sampling belt.

Figure 4:
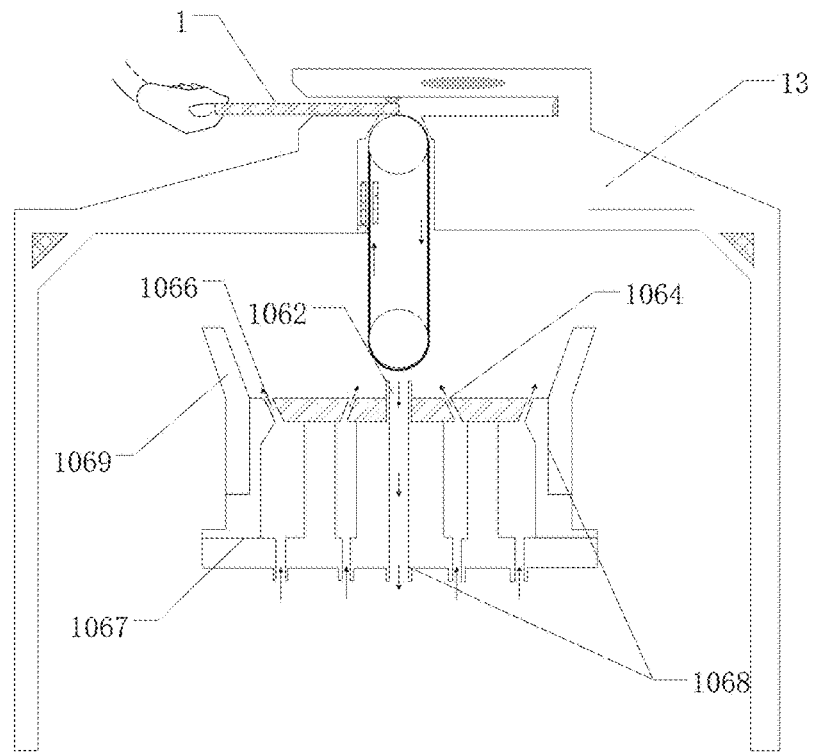
FIG. 4 illustrates a schematic diagram of a sampling apparatus in the gate system for sample detection according to an exemplary embodiment.

FIG. 4 illustrates a schematic diagram of a sampling apparatus in the gate system for sample detection according to an exemplary embodiment. As shown in FIG. 4, the inspiratory sampling apparatus 106 includes a sampling inspiratory port 1062, a central rotary (swirling) airflow discharge port 1064 and a peripheral rotary airflow discharge port 1066, a sampling head 1068, an O-ring seal 1067, and a flared sampling head cover 1069.

The sampling inspiratory port 1062 is provided under the wipe sampling apparatus 104, and is configured to draw the samples into the sampling apparatus.

The airflow discharge ports are configured to form airflows, and the airflow discharge ports include the central rotary airflow discharge port 1064 and the peripheral rotary airflow discharge port 1066.

The sampling head 1068 is configured to collect the samples, and the inspiratory sampling apparatus 106 includes a tornado sampling apparatus. The inspiratory sampling apparatus 106 may further include, for example, a thermal desorption chamber/cavity, and other sampling means/sampling modes such as a conventional inspiratory sampling pump (with an inspiratory sampling mode), and so on. The present disclosure will not be limited hereto.

The inspiratory sampling apparatus further includes the O-ring seal 1067 and the flared sampling head cover 1069.

In an exemplary embodiment of the present disclosure, the detection apparatus 108 includes a sample exchange semi-permeable membrane, a chromatographic column, and an ion migration tube. The sampling detection apparatus may use, for example, any kind and type of detection apparatus in the prior art to implement proper sampling to the samples. The present disclosure will not be limited hereto.

In this exemplary embodiment, the semi-permeable membrane is a film that only allows diffusion in and out of certain molecules or ions, with selectivity for the passage of different particles. For example, the cell membrane, the bladder membrane, the parchment, and artificial cotton films. Modern semipermeable membranes are also configured with porous walls, and made by precipitating appropriate compounds within their pores. In the present disclosure, the sample exchange semipermeable membrane may be any one or a combination of two or more of those semipermeable membranes as mentioned above. The present disclosure will not be limited hereto.

In this embodiment, the chromatographic column may be divided into two categories, i.e., the packed column and the open-tubular column, which are mostly made of metal or glass with a shape of a straight tube, a coil tube, a U-tube, etc. A liquid chromatography commonly uses the packed column. The chromatographic column may be divided into analytical type and preparative type according to the purposes thereof, among which the sizes/dimensions and specifications are different: ① a conventional analytical column (constant column), having an inner diameter in a range from 2 mm to 5 mm, and a column length in a range from 10 cm to 30 cm; ② a narrow bore, having an inner diameter in a range from 1 mm to 2 mm, and a column length in a range from 10 cm to 20 cm; ③ a micro column, having an inner diameter in a range from 0.2 mm to 0.5 mm; ④ a semi-preparative column, having an inner diameter larger than 5 mm; ⑤ a laboratory preparation column, having an inner diameter is within a range from 20 mm to 40 mm, and a column length in a range from 10 cm to 30 cm; ⑥ a production preparation column, the inner diameter of which may be up to several tens of centimeters. The inner diameter of the column is generally determined by the length of the column, the particle size of stuffing, and a reduced flow rate in order to avoid a wailer effect. In the present disclosure, the chromatographic column may be combination of any one or a combination of several columns as mentioned above. The present disclosure will not be limited hereto.

In the embodiment, the ion migration tube is a key component in calculation of ion mobility spectra. In the ion migration tube, ions fly under the action of an electric field force and collide with migration gas, so that the ions with different spatial sizes are separated, then arrive at the detection apparatus one after the other. In the present disclosure, the ion migration tube may be a combination of any kind and type in the prior art, and the present disclosure will not be limited hereto.

As mentioned above, substances such as drugs, explosives, etc. have higher boiling points and are not easily volatilized. When the drugs and the explosives are sampled by means of an inspiratory method, it is necessary to heat the ticket to be detected (on which the drugs or the explosives are adhered) to a certain temperature (above 80° C.), thereby prompt volatilization of the drugs or the explosives to obtain a satisfactory sampling result. However, each of the IC card and the ID card has a built-in chip, as well as a main body of plastic. High temperature may not only cause deformation of the cards but also damage the chips. For the drugs and the explosives, the use of wipe sampling means exhibits a better effect. In the present disclosure, the ticket to be detected is wiped by the wipe sampling belt 1042 to allow the samples to be adsorbed onto the belt, then the wipe sampling belt 1042 is struck by a high-temperature rotating airflow in the inspiratory sampling apparatus 106 to vaporize the samples, after that, the samples are brought via a tornado inspiratory sampling port in the inspiratory sampling apparatus 106, to pass the sample exchange semi-permeable membrane in the detection apparatus 108, and are subjected to detect and analyze with the chromatographic column and the ion migration tube.

Figure 5:
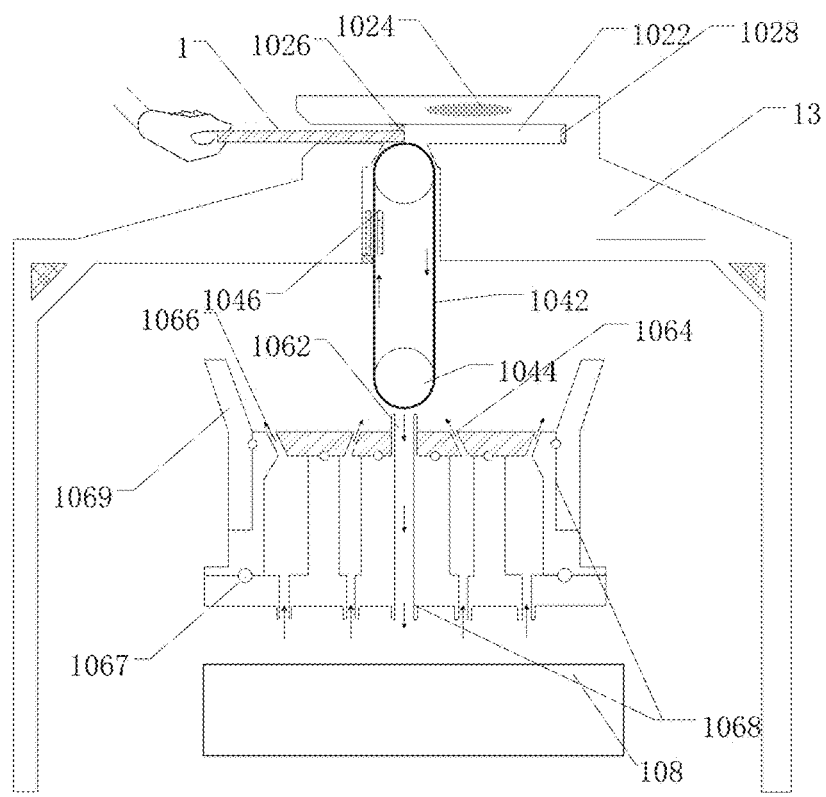
FIG. 5 illustrates a schematic diagram of a gate system for sample detection according to another exemplary embodiment.

FIG. 5 illustrates a schematic diagram of a gate system for sample detection according to another exemplary embodiment. As shown in FIG. 5, the operation process of the gate system for sample detection 10 may be, for example, as the follows.

The person to be passed through the gate inserts the ticket/IC card/ID card 1 into a bayonet of the card slot 1022 for the ticket to be detected. The spring top bead 1026, which is provided on one side of the bayonet, can force the ticket/IC card/ID card 1 to be in good contact with the wipe sampling belt 1042. The wipe sampling belt 1042 is transmitted by the drive of the electric roller 1044. At the same time, the wipe sampling belt 1042 will further drive the ticket/IC card/ID card 1 to move synchronously. The information reader 1024 for the ticket to be detected reads and verifies the information of the ticket to be detected. After the ticket/IC card/ID card 1 come contacted with the spring plate 1028 located at the end of the card slot 1022, the spring plate 1028 pops up the ticket/IC card/ID card 1 from the card slot. The passenger/related person can take out the ticket/IC card/ID card 1. At this time, a wipe-sampling process to the ticket/IC card/ID card 1 of the passenger/related person ends.

And, the wipe sampling belt 1042, to which samples from the document are adsorbed, continues to be transmitted by the drive of a motor, and passes over the tornado sampling device. An outer surface of the sampling head 1068 is provided with a heating film, and the outside of the heating film is coated with thermal insulation cotton. Purified air or purified nitrogen, incoming from four air inlet ports at the lower end of the tornado sampling device respectively, is heated via an inner chamber and an outer chamber, and then is discharged in a rotational way from the central rotary airflow discharge port 1064 and the peripheral rotary airflow discharge port 1066 respectively. Here, it is the high-flow high-speed rotating airflow that is discharged through the peripheral rotary airflow discharge port 1066, which is mainly used to form a tornado partial negative pressure. And the other airflow discharged through the central rotary airflow discharge port 1064 is a low velocity, high temperature gas stream that is primarily used to heat the wipe sampling belt 1042 and force the samples to be desorbed. Here, in order to enhance negative pressure effect of the tornado, the flared sampling head cover 1069 is provided on the upper part of the tornado sampling device, and the flared sampling head cover 1069 can focus the cyclone to enhance the negative pressure effect of the tornado. The O-ring seal 1067 is used for fixing between the flared sampling head cover 1069 and the tornado sampling device. The precipitated samples are analyzed through the semi-permeable membrane, the chromatographic column and the ion migration tube of the detection apparatus 108, under the effect of the negative pressure of the tornado sampling device and the suction of a sampling inspiratory pump below the sampling inspiratory port 1062.

The gate system for sample detection according to the present disclosure has a wide application range and can perform rapid sampling and detection of substances which are difficult to be volatilized. It is suitable for on-site rapid inspection at personnel access of airports/roads/railway gates, large-scale conferences, etc. It compensates for the problems of difficulty of sampling the substances such as the drags and the explosives which are difficult to be volatilized with poor detection accuracy in traditional sampling methods. It creates a new model for the inspection of trace substances.

It will be understood by those skilled in the art that the above-mentioned various of modules may be distributed in the apparatus according to the description of the embodiments, or may be changed correspondingly in one or more apparatuses different from the present embodiments. The modules of the above-mentioned embodiments may be combined into one module, or may be further split into multiple sub-modules.

Figure 6:
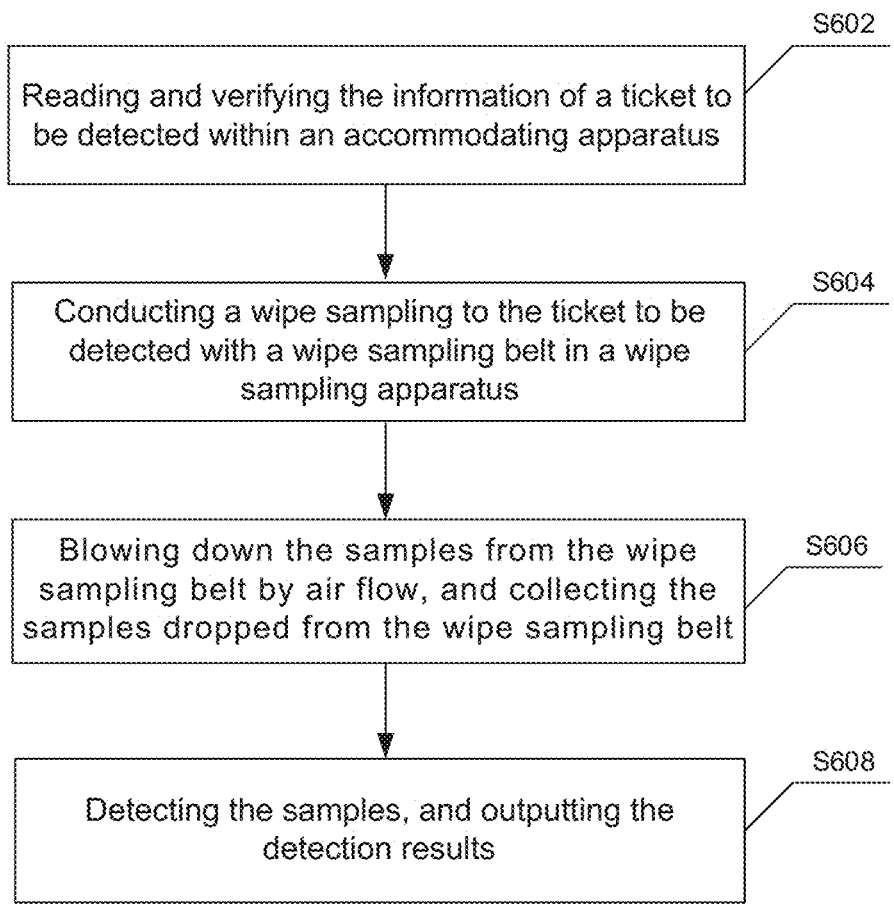
FIG. 6 illustrates a flow chart for a method of sample inspection according to an exemplary embodiment.

FIG. 6 illustrates a flow chart of a method of sample inspection according to an exemplary embodiment.

As shown in FIG. 6, in S602, information of the ticket to be detected within the accommodating apparatus is read and verified by the gate system. The gate system for sample detection includes an accommodating apparatus configured to read and verify the information of the ticket to be detected within the accommodating apparatus; a wipe sampling apparatus including a wipe sampling belt configured to drive the ticket to be detected to move within the accommodating apparatus, and to wipe and sample on the ticket to be detected; a sampling apparatus configured to collect samples dropped from the wipe sampling apparatus; and a detection apparatus configured to detect the samples and to output detection results.

In S604, the ticket to be detected is wiped and sampled by the wipe sampling belt in the wipe sampling apparatus.

In S606, the samples are blown down from the wipe sampling belt by air flow, and the samples dropped from the wipe sampling belt are collected.

In S608, the samples are detected, and the detection results are output.

According to the method for sample inspection of the present disclosure, a combination of a wipe sampling method with a better sampling effect especially on those highly boiling samples which are difficult to be volatilized, and a tornado sampling method with a higher sampling and collecting efficiency for gas samples, are used. The combination of these two sampling methods on the one hand avoids the risk of damage (due to direct heating) to documents/certificates, such as IC cards and ID cards. And on the other hand, in comparison to a traditional thermal analysis and inspiratory sampling method, the use of a tornado sampling device may not only simplify the design, but also present a better sample collection effect than a traditional inspiratory method.

It should be clearly understood that the present disclosure describes how to make and use particular examples, whereas the principles of the present disclosure will not be limited to any details of these examples. Rather, the principles can be applied to many other embodiments based on the teaching of the present disclosure herein.

Those skilled in the art will appreciate that all or part of the steps to implement the above-described embodiments are implemented as a computer program executed by a CPU. When the computer program is executed by the CPU, those functions defined by the above-mentioned methods provided by the present disclosure are performed. The program may be stored in a computer readable storage medium, which may be a read only memory, a magnetic disk or an optical disk, etc.

Furthermore, it should be noted that the above-described drawings are merely illustrative of the processes included in the methods according to the exemplary embodiments of the present disclosure, and are not intended to be limiting. It is easy to understand that the processes shown in the above drawings does not indicate or limit the chronological order of these processes. In addition, it is also easy to understand that these processes may be performed synchronously or asynchronously, for example, in a plurality of modules.

Through the description of the above embodiments, those skilled in the art will readily understand that the exemplary embodiments described herein may be implemented by software, or by software in combination with necessary hardware. Therefore, the technical solutions according to embodiments of the present disclosure may be embodied in the form of a software product, which may be stored in a non-volatile storage medium (which may be a CD-ROM (Compact Disk-Read Only Memory), a USB (Universal Serial Bus) flash drive, a mobile hard disk drive, etc.) or on a network, and a number of instructions may be included to allow a computing device (which may be a personal computer, server, terminal device, or network device, etc.) to perform a method in accordance with embodiments of the present disclosure.

The exemplary embodiments of the present disclosure have been specifically illustrated and described above. It should be understood that the present disclosure will not be limited to any detailed structures, arrangements, or implementations described herein. Rather, the present disclosure is to cover various modifications and equivalent settings included in the spirit and scope of the appended claims.

In addition, the structures, ratios, sizes, or the like, in the accompany drawings attached to the present specification, are only used to match with the contents disclosed in the specification for those skilled in the art for understanding and reading, and are not intended to limit the conditions under which the present disclosure can be implemented, and thus have no technical substantive significance. Any modifications of the structures, changes of the proportional relationship, or adjustment of the sizes, will still fall within the scope of the technical disclosure of the present disclosure, without departing from technical effects and achievable objectives of the present disclosure. Meanwhile, the terms "upper", "first", "second", and "one" that are referenced in the description, are only for the sake of narratively clarity, rather than for the purpose of limiting the scope of implementation of the present disclosure. The Change or adjustment of its relative relationship should also be considered to be within the scope of the present disclosure without any substantial change in the technical content.

What is claimed is:

1. A gate system for sample detection, comprising:
    an accommodating apparatus configured to accommodate a ticket to be detected the accommodating apparatus comprising a card slot configured to accommodate the ticket to be detected;
    a wipe sampling apparatus including a wipe sampling belt, the wipe sampling belt being configured to drive the ticket to be detected to move within the accommodating apparatus and to conduct a wipe sampling on the ticket to be detected;
    an inspiratory sampling apparatus configured to blow off samples from the wipe sampling apparatus by air flow at a high-temperature capable of vaporizing the samples to vaporize the samples and to collect the vaporized samples through cyclone;
    a detection apparatus configured to detect the samples and output detection results,
    an information reader configured to read information of the ticket to be detected by a chip built in the information reader, and to verify the information of the ticket; and
    a spring plate configured to remove the ticket from the card slot after the verification of the information of the ticket is completed,
    wherein the inspiratory sampling apparatus comprises:
    a sampling inspiratory port provided under the wipe sampling apparatus, and configured to draw the samples into the inspiratory sampling apparatus;
    airflow discharge ports configured to form airflows; and
    a sampling head configured to collect the samples,
    wherein the airflow discharge ports comprise a peripheral rotary airflow discharge port configured to discharge airflow to form a partial negative pressure, and a central rotary airflow discharge port configured to discharge airflow to heat the wipe sampling belt and force the samples to be desorbed.

2. The gate system according to claim 1, wherein the accommodating apparatus comprises:
    an elastically loaded protrusion configured to increase a contact pressure between the ticket to be detected and the wipe sampling belt such that the ticket to be detected becomes in contact with the wipe sampling belt.

3. The gate system according to claim 1, wherein the wipe sampling apparatus further comprises:
    an electric roller configured to drive the wipe sampling belt for transmission; and
    a semiconductor refrigeration chip configured to cool the wipe sampling belt.

4. The gate system according to claim 1, wherein the central rotary airflow discharge port is positioned outside of the sampling inspiratory port for discharging an airflow with a first flow rate; and the peripheral rotary airflow discharge port is positioned outside of the central rotary airflow discharge port for discharging an airflow with a second flow rate higher than the first flow rate.

5. The gate system according to claim 4, wherein the inspiratory sampling apparatus further comprises an O-ring seal and a flared sampling head cover.

6. The gate system according to claim 1, wherein the inspiratory sampling apparatus comprises a cyclone sampling apparatus.

7. The gate system according to claim 1, wherein the detection apparatus comprises:

at least one of a chromatographic column and an ion migration tube, and a sample exchange semi-permeable membrane.

8. A method of sample inspection, comprising:
receiving a ticket to be detected;
conducting a wipe-sampling to the ticket to be detected with a wipe sampling belt in a wipe sampling apparatus;
blowing off samples from the wipe sampling belt by air flow at a high-temperature capable of vaporizing samples to vaporize the samples, and collecting the vaporized samples through cyclone effect;

detecting the samples and outputting detection results;

after receiving the ticket to be detected, reading and verifying information of the ticket to be detected within an accommodating apparatus by a gate system; and removing the ticket from a card slot by a spring plate after the verification of the information of the ticket is completed, wherein the gate system comprises:

the spring plate configured to remove the ticket from the card slot after the verification of the information of the ticket is completed; and the accommodating apparatus configured to accommodate the ticket to be detected, the accommodating apparatus comprising the card slot configured to accommodate the ticket to be detected, an inspiratory sampling apparatus configured to blow off samples from the wipe sampling apparatus by air flow and to collect the samples blown from the wipe sampling belt;

wherein the inspiratory sampling apparatus comprises:

a sampling inspiratory port provided under the wipe sampling apparatus, and configured to draw the samples into the inspiratory sampling apparatus;

airflow discharge ports configured to form airflows; and a sampling head configured to collect the samples, wherein the airflow discharge ports comprise a peripheral rotary airflow discharge port configured to discharge airflow to form a partial negative pressure, and a central rotary airflow discharge port configured to discharge airflow to heat the wipe sampling belt and force the samples to be desorbed.

9. The method according to claim 8, wherein the gate system further comprises:

the wipe sampling apparatus including the wipe sampling belt, the wipe sampling belt is configured to drive the ticket to be detected to move within the accommodating apparatus and to conduct the wipe-sampling to the ticket to be detected; and a detection apparatus configured to detect the samples and output the detection results.

* * * * *